(12) United States Patent
Kong et al.

(10) Patent No.: US 7,008,970 B2
(45) Date of Patent: Mar. 7, 2006

(54) METHOD FOR DIRECT CONVERSION OF GASEOUS HYDROCARBONS TO LIQUIDS

(75) Inventors: Peter C. Kong, Idaho Falls, ID (US); Paul A. Lessing, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 11/176,730

(22) Filed: Jul. 6, 2005

(65) Prior Publication Data

US 2005/0241994 A1 Nov. 3, 2005

Related U.S. Application Data

(62) Division of application No. 10/057,543, filed on Jan. 23, 2002.

(51) Int. Cl.
C07C 27/00 (2006.01)
C07C 1/02 (2006.01)
C07B 41/02 (2006.01)

(52) U.S. Cl. .................. 518/728; 568/910.5; 252/373; 518/700

(58) Field of Classification Search ................ 518/728, 518/700; 568/910.5; 252/373
See application file for complete search history.

(56) References Cited

U.S. PATENT DOCUMENTS

| 5,427,747 A | 6/1995 | Kong et al. |
| 5,939,031 A * | 8/1999 | Ellis et al. .................. 422/191 |
| 6,087,405 A | 7/2000 | Plecha et al. |
| 6,117,814 A | 9/2000 | Plecha et al. |
| 6,124,367 A | 9/2000 | Plecha et al. |

OTHER PUBLICATIONS

Chang et al., "EHD Surface Waves of Diesel Oil Thin Films Generated by Wire-Plate Barrier Discharges," 1997 IEEE Annual Report—Conference On Electrical Insulation And Dielectric Phenomena, Minneapolis, Oct. 19-22, 1997.
Park, et al., "Generation of atmospheric pressure plasma with a dual-chamber discharge," Applied Physics Letters, vol. 77, No. 14, Oct. 2, 2000.
Urashima et al., "The Effect of Gravity Direction on the EHD Surface Waves of Dielectric Oil Thin Films Generated by Wire-Plate Barrier Discharges," IEEE 1998.

* cited by examiner

*Primary Examiner*—J. Parsa
(74) *Attorney, Agent, or Firm*—Trask Britt, P.C.

(57) ABSTRACT

A chemical reactor for direct conversion of hydrocarbons includes a dielectric barrier discharge plasma cell and a solid oxide electrochemical cell in fluid communication therewith. The discharge plasma cell comprises a pair of electrodes separated by a dielectric material and passageway therebetween. The electrochemical cell comprises a mixed-conducting solid oxide electrolyte membrane tube positioned between a porous cathode and a porous anode, and a gas inlet tube for feeding oxygen containing gas to the porous cathode. An inlet is provided for feeding hydrocarbons to the passageway of the discharge plasma cell, and an outlet is provided for discharging reaction products from the reactor. A packed bed catalyst may optionally be used in the reactor to increase efficiency of conversion. The reactor can be modified to allow use of a light source for directing ultraviolet light into the discharge plasma cell and the electrochemical cell.

18 Claims, 6 Drawing Sheets

METHOD FOR DIRECT CONVERSION OF GASEOUS HYDROCARBONS TO LIQUIDS

RELATED APPLICATIONS

This application is a divisional of pending U.S. patent application Ser. No. 10/057/543, filed Jan. 23, 2002 and is incorporated herein by reference.

CONTRACTUAL ORIGIN OF THE INVENTION

The United States Government has certain rights in this invention pursuant to Contract No. DE-AC07-99ID13727, and Contract No. DE-AC07-05ID14517 between the United States Department of Energy and Battelle Energy Alliance, LLC.

BACKGROUND OF THE INVENTION

1. Field of the Invention

This invention relates to techniques for direct conversion of hydrocarbons from a gaseous form to a liquid form. More particularly, the invention relates to methods and apparatus for reactive conversion of hydrocarbons, such as direct natural gas to liquid conversion.

2. Background Technology

Methane is an abundant hydrocarbon fuel and chemical feed stock, and is expected to remain so for quite some time. Yet, because of capital and technological barriers, methane has remained an under-utilized resource throughout the world. It is desirable to upgrade available methane to methyl or higher oxygen atom containing hydrocarbons, such as alcohols, ethers, aldehydes, etc. Existing technologies for converting methane to methanol include destruction of methane to form a synthesis gas ($H_2$ and CO), followed by indirect liquefaction steps.

Conventional catalytic approaches to produce methanol from methane typically have poor conversion efficiencies, slow reaction rates, and are not economically competitive because they are typically so energy intensive. One such process, the oxidative coupling process, involves the use of oxidants to abstract hydrogen from methane, and coupling two or more hydrocarbon radicals to form light olefins, oxygenates, and other hydrocarbons. The oxidants are oxygen, halogens and reducible metal oxides as oxygen carriers and catalysts. In the oxidative coupling process, hydrogen abstraction at the oxygen centers of the catalyst is typically the rate-determining step, and catalyst properties are important for end product selectivity. Therefore, the maximum rate of product conversion strongly depends on the rate of radical formation on the active oxygen centers. In order to increase the rates, chemists have used high temperatures, even in excess of 900° C. However, this undesirably promotes deep oxidation of methane to fully oxidized species, such as $CO_2$.

In another approach, a high temperature dehydrogenation coupling process is employed that has a very high radical generation rate, and correspondingly a high rate of light olefin formation. However, this process is plagued by solid carbon formation which lowers the efficiency of the olefin production, and excess hydrogen is necessary to suppress the solid carbon formation.

In U.S. Pat. No. 5,427,747 to Kong et al. (hereinafter "Kong"), the disclosure of which is incorporated herein by reference, a method for producing oxygenates from hydrocarbons is described that utilizes a chemical reactor for oxygenating hydrocarbons. The chemical reactor includes a dielectric barrier discharge plasma cell which includes a pair of electrodes having a dielectric material and void therebetween, and a hydrocarbon gas inlet feeding to the void. The reactor also has a solid oxide electrochemical cell (SOEC) that includes a solid oxide electrolyte positioned between a porous cathode and a porous anode, and an oxygen containing gas inlet stream feeding to the porous cathode side of the electrochemical cell. A first gas passageway feeds from the void to the anode side of the electrochemical cell. A gas outlet feeds from the anode side of the electrochemical cell to expel reaction products from the chemical reactor.

In another technique for gas to liquid conversion, an apparatus is employed that uses a high temperature ionic conducting electrolyte membrane plate for oxygen anion diffusion. A porous cathode and a porous anode are attached on opposite surfaces of the electrolyte plate. An inert ceramic tube is bonded to the electrolyte plate to form an SOEC cell structure. The SOEC cell must use an external power source for operation.

Other approaches include the so-called Fischer-Tropsch and other indirect processes for liquid production from natural gas. These processes rely on steam reforming or partial oxidation of natural gas to synthesis gas, and use high temperatures, high pressures, and catalysis. The Fischer-Tropsch processes have the disadvantages of being capital and energy intensive, having low overall production yield of liquid, and requiring multiple passes to get a desirable liquid yield.

Accordingly, it would be desirable to provide improved apparatus and methods for converting gas to liquids that avoids or overcomes the difficulties and problems of prior techniques.

SUMMARY OF THE INVENTION

The present invention contemplates both systems and methods for reactive conversion of hydrocarbons, such as gas to liquid conversion of hydrocarbons. The systems and methods utilize a chemical reactor that includes a dielectric barrier discharge plasma cell and a solid oxide electrochemical cell in fluid communication therewith. In one embodiment, the dielectric barrier discharge plasma cell comprises a pair of electrodes separated by a dielectric material and passageway therebetween. The electrochemical cell comprises a mixed-conducting solid oxide electrolyte membrane tube positioned between a porous cathode and a porous anode, and a gas inlet tube for feeding oxygen containing gas to the porous cathode. An inlet is provided for feeding hydrocarbons to the passageway of the discharge plasma cell, and an outlet is provided for discharging reaction products from the reactor. A packed bed catalyst can optionally be used in the reactor to increase efficiency of conversion.

In another embodiment of the invention, a chemical reactor includes a dielectric barrier discharge plasma cell and a solid oxide electrochemical cell in fluid communication therewith. In addition, this reactor is adapted to be used with an ultraviolet (UV) light source, which can be positioned within an electrode of the discharge plasma cell. The electrode is constructed to allow transmission of UV light into the reactor. A packed bed catalyst can optionally be used in the reactor along with the light source to increase efficiency of conversion.

The systems and methods of the invention can be used to convert gaseous hydrocarbons such as natural gas to various liquid products, and allow for the conversion of oil field associated gases to liquid products. The reaction products can include transportation fuel components such as gasoline or diesel fuel, and commodity chemicals such as alcohols. The present invention eliminates the problems of conventional conversion processes and can achieve significant gas conversion and liquid yield in a single step. The present invention also enhances the rate of methane activation for conversion to liquid oxygenated hydrocarbons and other light fuels.

These and other features and advantages of the present invention will become more fully apparent from the following description and appended claims, or may be learned by the practice of the invention as set forth hereinafter.

BRIEF DESCRIPTION OF THE DRAWINGS

In order to illustrate the manner in which the above recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE INVENTION

The present invention is directed to systems and methods for reactive conversion of hydrocarbons, such as converting gaseous hydrocarbons (e.g., natural gas) to various liquid products. The liquid products produced can include transportation fuel components such as gasoline or diesel fuel, and commodity chemicals such as alcohols. The systems and methods of the present invention also allow for the conversion of oil field associated gases ($C_1$ to $C_4$) to liquid products.

Figure 1:
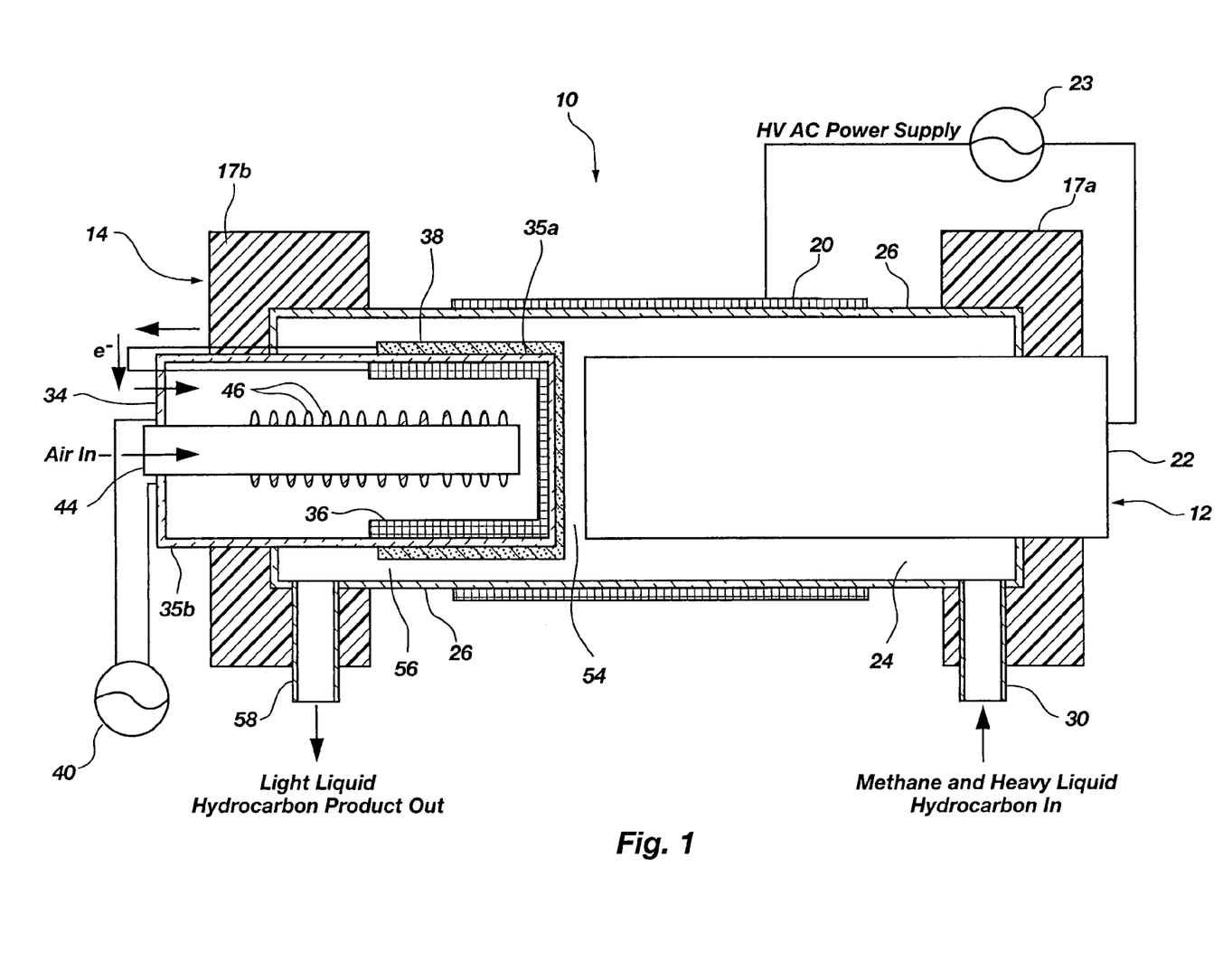
FIG. 1 is a schematic cross-sectional view of an apparatus for reactive conversion of hydrocarbons in accordance with one embodiment of the invention.

Referring to the drawings, wherein like structures are provided with like reference designations, FIG. 1 depicts a chemical reactor 10 used for gas to liquid conversion of hydrocarbons. The reactor 10 generally comprises a longitudinally elongated dielectric barrier discharge plasma cell 12, and a solid oxide electrochemical cell 14. The plasma cell 12 and electrochemical cell 14 are preferably positioned between opposing end caps 17a and 17b. However, one skilled in the art will recognize that a common housing may be employed that is integrally formed without distinct parts.

For purposes of the discussion hereafter, the facing ends of plasma cell 12 and electrochemical cell 14 will be considered facing in the inward direction, while the opposing ends of the respective cells will be considered facing in the outward direction.

The discharge plasma cell 12 comprises an outer electrode 20 and an inner electrode 22 which are operatively connected to a power supply 23. The outer electrode 20 can take the form of an elongated metal cylindrical screen shell which is partially surrounding and supported by a support tube 26. Suitable materials of construction for outer electrode 20 are stainless steel, and the like. The inner electrode 22 can take the form of an elongated rod member, which can be either solid or hollow. The inner electrode 22 is disposed concentrically internal of outer electrode 20 and within support tube 26. Suitable materials of construction for inner electrode 22 are stainless steel, titanium, nickel, gold, and the like. In an alternative embodiment, inner electrode 22 can be constructed of a catalytic material or can have a catalyst material coating thereon, which is discussed more fully hereafter. The outer electrode 20 also extends longitudinally inwardly beyond the inward end of electrode 22 such that electrode 20 covers the inward end of electrochemical cell 14. The electrode 22 is centrally positioned within support tube 26 to define a central axis of plasma cell 12.

The support tube 26 provides a barrier layer and is formed of a dielectric material. The support tube 26 can be composed of a ceramic oxide material such as quartz, as well as zirconia, alumina, glass, and the like. A first passageway 24 in the shape of an elongated annulus is defined between support tube 26 and electrode 22. A hydrocarbon gas inlet feed 30 extends from the exterior of housing end cap 17a to annular passageway 24.

The solid oxide electrochemical cell 14 comprises a mixed-conducting solid oxide electrolyte membrane tube 34. The electrolyte membrane tube 34 is defined as "mixed-conducting" because it conducts both ionically and electronically. The electrolyte membrane tube 34 has a closed inward end 35a and an opened outward end 35b as indicated in FIG. 1. Positioned on a portion of the exterior of electrolyte membrane tube 34 toward inward end 35a is a porous anode 38. Likewise, a porous cathode 36 is positioned on a portion of the interior of electrolyte membrane tube 34 opposite porous anode 38 such that electrolyte membrane tube 34 encompasses cathode 36 therewithin.

One skilled in the art will appreciate that electrolyte membrane tube 34 provides for increased surface area for chemical reactions depending on the extent to which electrolyte membrane tube 34 is coated with anode and cathode material. Furthermore, those skilled in the art will recognize that many different materials can be used to provide the ionic and electronic conducting properties of electrolyte membrane tube 34. Mixed oxide ceramic materials that function at sufficiently low temperatures (e.g., about 300° C. to about 600° C.) are useful as electrolyte materials. One preferred electrolyte material used to form tube 34 is $CeO_2$ doped with CaO. Other suitable electrolyte materials include $SrCe_{0.95}Y_{0.05}O_{3-x}$, $BaCe_{0.9}Gd_{0.1}O_3$, $Sr_2Gd_2O_5$, ion exchanged β'' alumina, bismuth based oxides, and the like. In addition, the use of a mixed-conducting electrolyte is advantageous as it allows solid oxide electrochemical cell 14 to function without the need of a power supply.

The anode 38 preferably incorporates a catalyst material to facilitate formation of fuel-type products. Suitable catalyst materials for the anode 38 include silver, nickel, platinum, cobalt, doped $CaTiO_3$, $La_{0.85}Sr_{0.15}MnO_3$, $La_{0.85}Sr_{0.15}CrO_3$, and the like. The cathode 36 is preferably formed of a metal screen mesh, such as a mesh formed with elemental platinum or elemental silver.

As mentioned previously, electrode 22 can be constructed of a catalytic material or can have a catalyst material coating thereon, which enhances the formation of desired fuel products. Some metals are known to be catalytic to hydrocracking and hydrotreating of a hydrocarbon feed stream. Examples of these metals are cobalt (Co), nickel (Ni), platinum (Pt), rhenium (Re), molybdenum (Mo), tungsten (W), and palladium (Pd). These metals can be manufactured as single metal or bimetal fine powders supported on porous hollow cylinders and spheres of alumina, silica, or zeolite. These supported catalysts can be used for natural gas conversion to light liquids. Other examples of hydrocracking catalysts are NiMo, CoMo, and CoW. Examples of hydrotreating catalysts are Ni, Co, Pt, and Re.

There are various configurations which can be employed for a catalytic electrode. In one embodiment, electrode 22 can comprise a non-catalytic base metal (e.g., stainless steel) with single metal or bimetal catalysts deposited on the electrode surface as discrete nanoparticles for either hydrocracking or hydrotreating of the feed materials. Alternatively, two different metal catalysts can be zone deposited on the electrode surface as discrete nanoparticles for successive catalytic hydrocracking and hydrotreating of the feed materials. In another embodiment, electrode 22 can comprises a catalytic base metal with a second catalytic metal deposited on the electrode surface as discrete nano-particles. For example, the electrode can be fabricated from Co or Ni, and the second metal, such as Mo, W or Pt, is deposited on the electrode surface as discrete nanoparticles.

In yet another embodiment, electrode 22 can comprise a catalytic base metal with two other catalytic metals being zone deposited on the electrode surface as discrete nano-particles. This allows successive catalytic hydrocracking and hydrotreating of the feed materials because the different metals will produce different reactions. For example, the base metal can be fabricated from Co or Ni, while one metal, for example Mo, is deposited in a first zone proximal to the feed source, and a second metal, for example W, is deposited in a second zone on the electrode distal from the feed source.

One skilled in the art will recognize that a variety of configurations may be suitably employed to perform the functions set forth herein for a catalytic electrode. The single metal and bimetal catalytic design for configuring electrode 22 are only illustrative and should not be construed as limiting the scope of the present invention.

A distinct advantage of the present invention is that it does not require an external power source to operate the solid oxide electrochemical cell 14. Rather, the solid oxide electrochemical cell 14 is internally short-circuited, i.e., electrons and $O^{2-}$ anions diffuse internally in the material in opposite directions. However, an optional external electromotive force generator 40, such as a variable voltage battery or generator may be used to complete the electronic or electrical circuit. Such can be used to enhance the driving of anions through the electrolyte.

An inner elongated gas inlet tube 44 is provided for feeding oxygen containing gas from the exterior of end cap 17b to the porous cathode side of electrolyte membrane tube 34. The inlet tube 44 is surrounded by a plurality of electric heating elements 46 for maintaining oxygen containing gas within tube 44 at a desired temperature condition.

The temperature of electrolyte membrane tube 34 may be controlled using a water jacket/ring as discussed and shown in U.S. Pat. No. 5,427,747 to Kong et al. (hereinafter the "Kong patent"), the disclosure of which is incorporated herein by reference. Furthermore, plasma cell 12 and electrochemical cell 14 may be axially positioned in end-to-end alignment using supporting structure as shown and discussed in the Kong patent.

The described arrangement for plasma cell 12 and electrochemical cell 14 defines an annular void 54 which feeds from passageway 24 to porous anode 38. A second gas passageway 56 is annularly defined about membrane tube 34, and feeds from void 54 and the anode side of electrochemical cell 14 to a product outlet 58 which expels reaction products from chemical reactor 10. Accordingly, product outlet 58 extends from passageway 56 to externally of endcap 17b. The passageway 24, void 54, and passageway 56 can be considered to comprise a single passageway allowing materials to flow from inlet 30 to product outlet 58.

Figure 2:
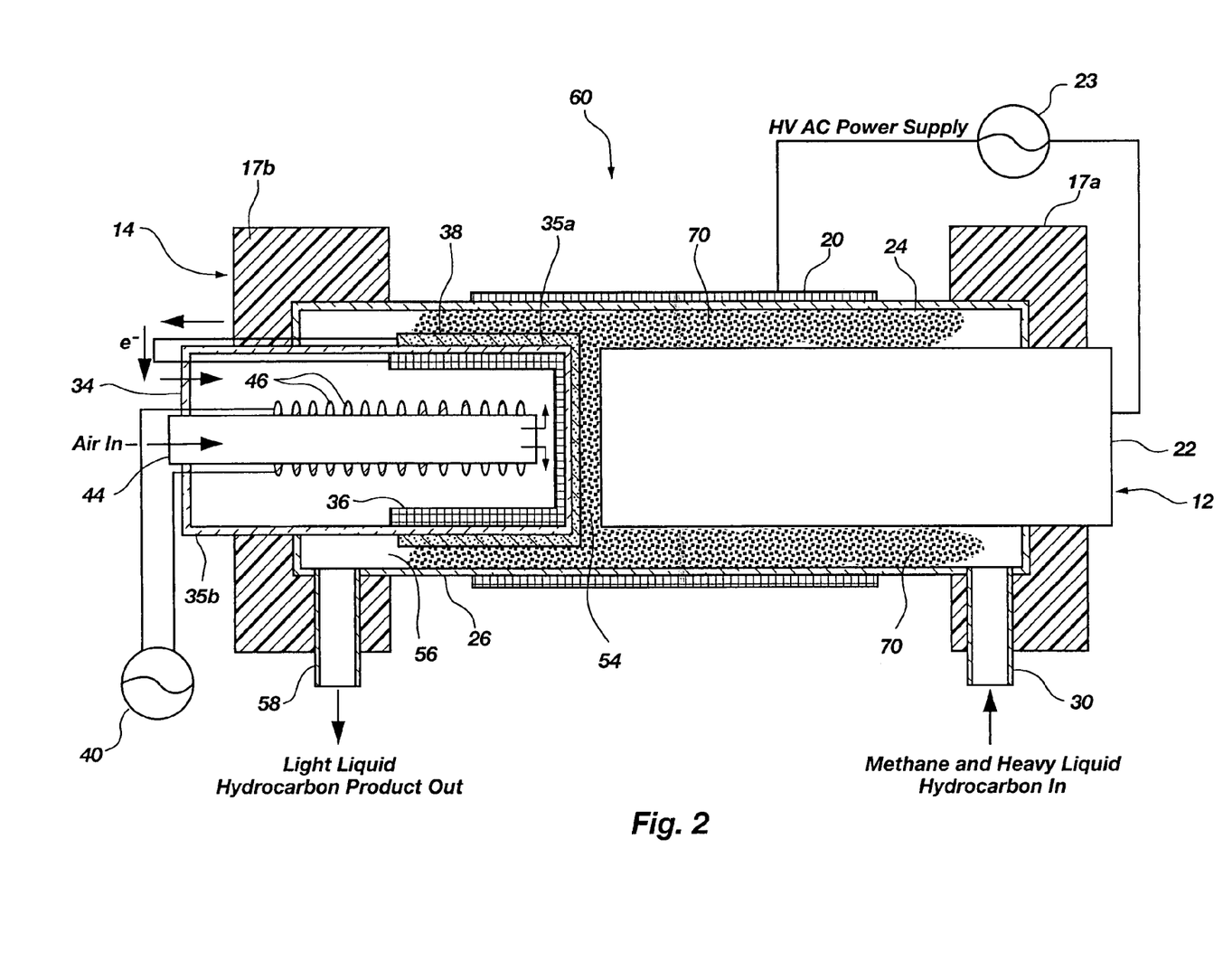
FIG. 2 is a schematic cross-sectional view of an apparatus for reactive conversion of hydrocarbons in accordance with another embodiment of the invention.

FIG. 2 depicts a chemical reactor 60 used for gas to liquid conversion of hydrocarbons according to another embodiment of the invention. The reactor 60 includes components similar to those discussed above with respect to reactor 10. Accordingly, reactor 60 generally comprises a dielectric barrier discharge plasma cell 12, and a solid oxide electrochemical cell 14. The plasma cell 12 and electrochemical cell 14 are preferably self-supported and positioned or enclosed between opposing end caps 17a and 17b.

The discharge plasma cell 12 comprises an outer electrode 20 and an inner electrode 22 which are operatively connected to a power supply 23. The outer electrode 20 partially surrounds and is supported by a support tube 26. The inner electrode 22 is disposed concentrically internal of outer electrode 20 and within support tube 26. A first passageway 24 is defined between support tube 26 and electrode 22. A hydrocarbon gas inlet feed 30 extends from the exterior of housing end cap 17a to annular passageway 24.

The solid oxide electrochemical cell 14 comprises a mixed-conducting solid oxide electrolyte membrane tube 34. The electrolyte membrane tube 34 has a closed inward end 35a and an opened outward end 35b. A porous anode 38 is positioned on the exterior of electrolyte membrane tube 34 at inward end 35a. A porous cathode 36 is positioned on the interior of electrolyte membrane tube 34 opposite porous anode 38. An optional external electromotive force generator 40 may be used to complete the electrolytic circuit and enhance the driving of anions through the electrolyte.

A gas inlet tube 44 is provided for feeding oxygen containing gas from the exterior of end cap 17b to the porous cathode side of electrolyte membrane tube 34. The inlet tube 44 is surrounded by a plurality of electric heating elements 46. An annular void 54 feeds from passageway 24 to porous anode 38. A second gas passageway 56 is annularly defined about membrane tube 34, and is in fluid communication with void 54 and a product outlet 58.

In addition, a packed bed catalyst 70 is disposed in reactor 60 within passageway 24, void 54, and passageway 56 as shown in FIG. 2. The packed bed catalyst 70 can be used to control the types of products that reactor 60 yields. Suitable materials for the packed bed catalyst include those appropriate for the catalytic electrode 22 discussed previously. Generally, any hydrocracking catalysts, hydrogenating catalysts, or a combination of these catalysts can be used for heavy oil and natural gas conversion. Under the influence of non-thermal plasma, the catalysts may have increased activity.

In one embodiment, the packed bed catalyst 70 may comprise a single catalytic zone configuration. This configuration includes a single catalyst component bed for either hydrocracking or hydrotreating of the feed material. In an alternative embodiment, the packed bed catalyst 70 may comprise a double zone configuration. This configuration includes alternating catalyst components for successive hydrocracking and hydrotreating of the feed material. It should be noted that a variety of configurations may be suitably employed to perform the functions set forth herein for the packed bed catalyst. The single zone and double zone configurations for packed bed catalyst 70 are only illustrative and should not be construed as limiting the scope of the invention. In addition, the packed bed catalyst may be used in conjunction with a catalytic anode, a catalytic electrode, or both.

During operation of chemical reactor 10 or reactor 60, a gaseous hydrocarbon feed, such as methane, is directed through inlet 30 into annular passageway 24. The gaseous feed is subjected to a dielectric barrier discharge generated between electrodes 20 and 22. Such a dielectric barrier discharge produces a non-equilibrium or "cold" plasma in which the electron temperature is typically very high (i.e., about $10^4$ K.), while the gas temperature remains at ambient (i.e., less than about 373 K.). Specifically, when a high voltage (i.e., about 1000 or greater AC/DC volts) is applied between electrodes 20 and 22, the dielectric barrier formed by dielectric support tube 26 effectively breaks down, enabling multiple discharges to be maintained between dielectric tube 26 and central electrode 22. The discharges are in the form of micro-arcs which induce dissociation and ionization of gases. The dissociation of gases in this type of discharge generates a high concentration of free radicals, in the plasma state, which are reactive at high rates. The operating conditions of a dielectric barrier discharge cell are discussed in the Kong patent previously incorporated herein by reference.

The free radicals formed within passageway 24 flow inwardly to void 54 and in close proximity and into porous anode 38. Accordingly, reactive hydrocarbon radicals are presented at porous anode 38. The outer cylindrical shell electrode 20 preferably extends beyond the inner end terminus of central electrode 22, as described above, to enable arcing and radical generation beyond the inner end terminus of central electrode 22 within void 54.

The solid oxide electrochemical cell 14 is operated in unison with the discharge plasma cell 12. Specifically, a gaseous oxygen containing species is fed to the porous cathode side of electrochemical cell 14. Examples of oxygen containing materials are air, $O_2$, or combinations thereof. The gaseous oxygen containing species is converted to oxygen anions at cathode 36. These anions are electrochemically driven through the electrolyte membrane tube 34 and discharge at and through anode 38 to provide a reactive oxygen species at the anode. Driving of anions can be enhanced by operating an external driving force such as electromotive force generator 40.

The reactive species will typically be in the form of the driven anions or oxygen containing radicals generated therefrom. Preferably, a reaction enhancing electrocatalytic effect is provided by solid oxide electrochemical cell 14. For example, in such instance, the material of anode 38 or the material of electrolyte membrane tube 34 can have catalytic sites. These catalytic sites significantly enhance the overall reaction by converting the driven anions into radicals or other activated species which react with the hydrocarbon radicals.

Thus, highly reactive oxygen containing species capable of reaction with hydrocarbon radicals are presented at porous anode 38 from the operation of solid oxide electrochemical cell 14. There, the hydrocarbon radicals formed by the dielectric barrier discharges combine with the oxygen anions, radicals and/or other activated species to form liquid products, such as methanol, gasoline, diesel, or other fuel products. The liquid products flow from second passageway 56 through product outlet 58.

The rate of oxidants supplied to anode 38 can be controlled via generator 40 (e.g., controlled power supply to regulate the voltage and current), which conducts excess electrons out of the anode. Such an approach is described in further detail in the Kong patent. Numerous possible reactions are involved in the dielectric barrier discharge and at the solid oxide electrochemical cell surface as described in the Kong patent.

Because the amount of oxidant radicals supplied to anode 38 can be finely controlled, higher overall conversions to liquid at a faster methane input flow rate can be achieved. This is because the system is not limited by long residence times or oxygen availability, since reactive oxygen is generated by purely electrochemical mechanisms or by a combination of electrochemical and electrocatalytic mechanisms. Ambient temperature operation of the discharge plasma cell 12 prevents solid carbon formation during the discharge because complete hydrogen abstraction from the hydrocarbon is not encouraged. Accordingly, there is a corresponding enhancement in the efficiency of liquid fuel formation.

The above-described method produces primary products of gasoline and diesel fuel. As minor products, the present method produces oxygenated products such as alcohol. The present method has been found to produce substantially no CO or $CO_2$ during the reaction process. Furthermore, excess hydrogen radicals are eliminated from the plasma as water molecules by reacting with oxygen radicals from solid oxide electrochemical cell 14.

Figure 3A:
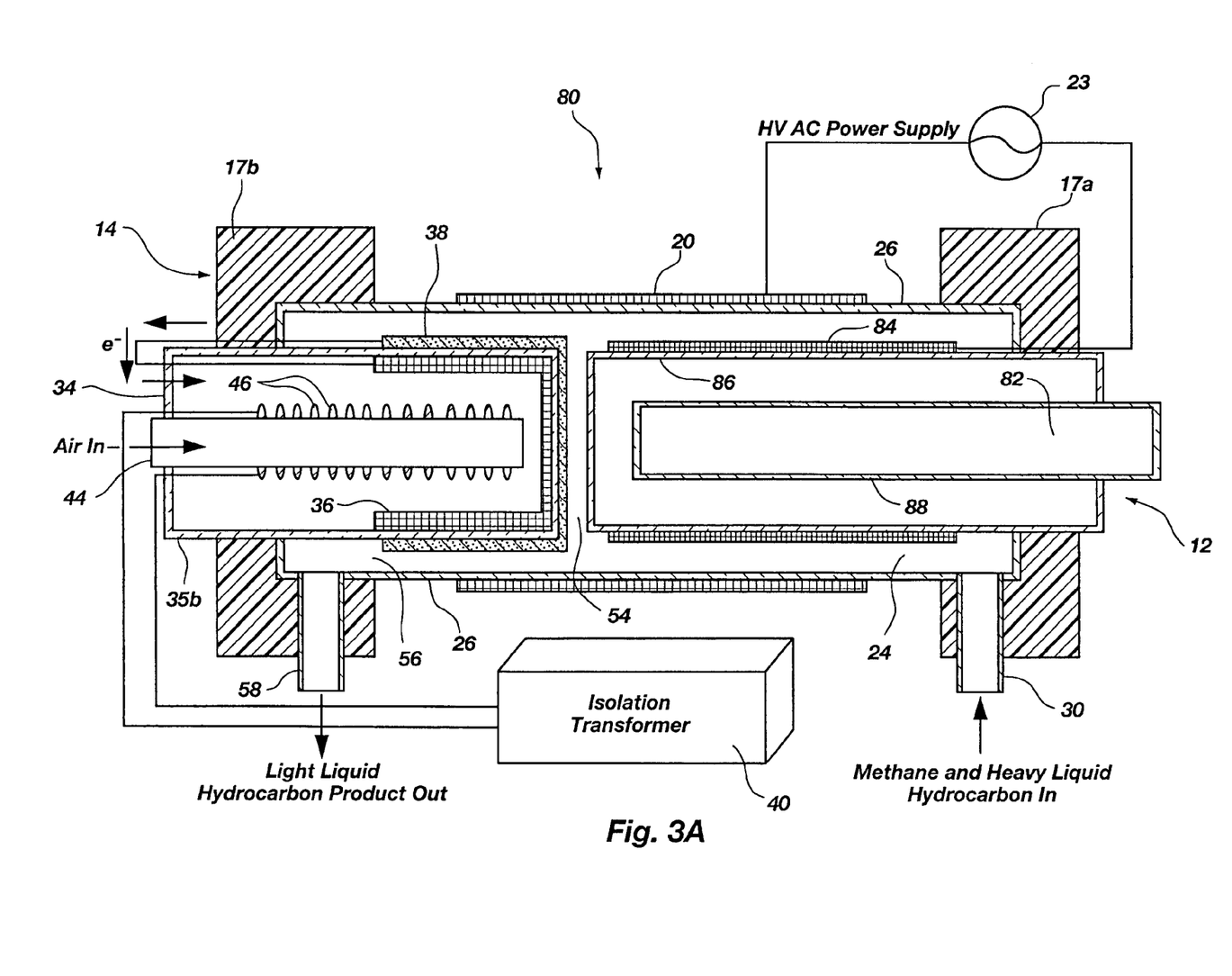
FIG. 3A is a schematic cross-sectional view of an apparatus for reactive conversion of hydrocarbons in accordance with an alternative embodiment of the invention.

In accordance with another embodiment of the invention, FIG. 3A illustrates a chemical reactor 80 that can be used for gas to liquid conversion of hydrocarbons. The reactor 80 includes components similar to those discussed above with respect to reactor 10, except that reactor 80 is adapted to be used with an ultraviolet (UV) light source 82. Thus, reactor 80 generally comprises a dielectric barrier discharge plasma cell 12, and a solid oxide electrochemical cell 14.

The discharge plasma cell 12 comprises an outer electrode 20 and an inner electrode 84 which are operatively connected to a power supply 23. The outer electrode 20 partially surrounds and is supported by a support tube 26. The inner electrode 84 is disposed internally of outer electrode 20 and within support tube 26. A first passageway 24 is defined between support tube 26 and electrode 84. A hydrocarbon gas inlet feed 30 extends from the exterior of the housing to annular passageway 24.

The solid oxide electrochemical cell 14 comprises a mixed-conducting solid oxide electrolyte membrane tube 34. A porous anode 38 is positioned on the exterior of electrolyte membrane tube 34. A porous cathode 36 is positioned on the interior of electrolyte membrane tube 34 opposite porous anode 38. An optional external electromotive force generator 40 may be used to complete the electrolytic circuit.

A gas inlet tube 44 is provided for feeding oxygen containing gas to the porous cathode side of electrolyte membrane tube 34. The inlet tube 44 is surrounded by a plurality of electric heating elements 46. An annular void 54 feeds from passageway 24 to porous anode 38. A second gas passageway 56 is annularly defined about membrane tube 34, and is in fluid communication with void 54 and a product outlet 58.

As shown in FIG. 3A, UV light source 82 can be positioned within electrode 84. The electrode 84 is constructed such that UV light can pass into passageway 24, void 54, and passageway 56. For example, electrode 84 can be constructed of a metallic screen shell. The electrode 84 can be constructed of the same materials as described for electrode 22 previously. A housing structure 86 may be used to support electrode 84 as shown in FIG. 3. The housing structure 86 is constructed of a transparent material, such as glass or quartz, such that UV light is permitted to pass through housing structure 86, past electrode 84 and into passageway 24. The UV light source 82 can also be contained within an additional housing structure 88. The housing structure 88 is also constructed of a transparent material such as glass or quartz to allow UV light to transmit through to the chemical reactor. One skilled in the art will recognize that housing structures 86 and 88 may be substituted with other configurations as needed. For example, other configurations may include electrode 84 without a supporting housing structure, while the UV light source may have a housing structure, or vice-versa.

Figure 3B:
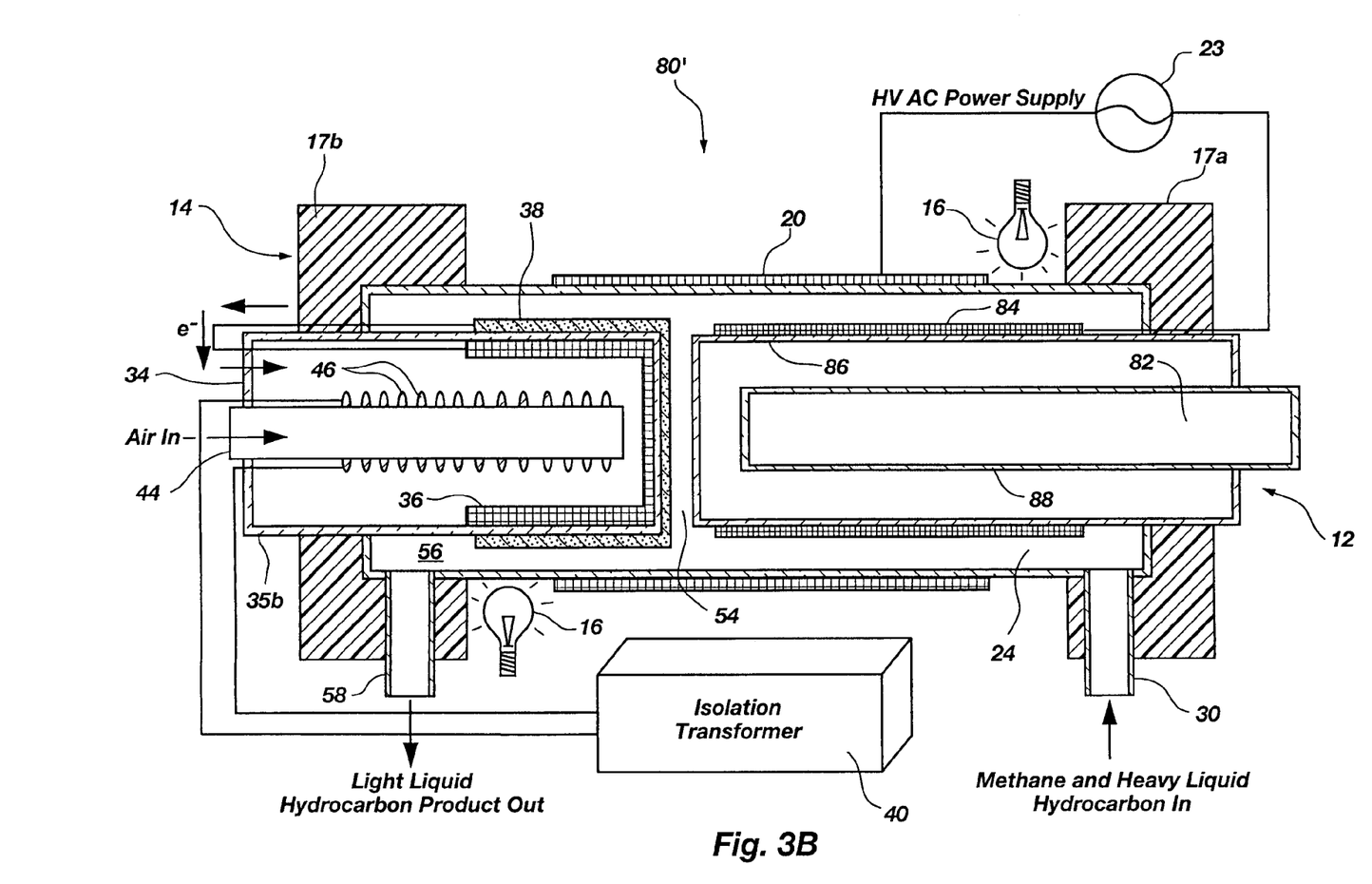
FIG. 3B is a schematic cross-sectional view of an apparatus for reactive conversion of hydrocarbons in accordance with another embodiment of the invention.

Alternatively, as depicted in FIG. 3B, a chemical reactor 80' can be provided with one or more UV light sources 16 which may be placed outside of the reactor housing when the reactor housing is UV transparent, allowing UV light to be transmitted into the reactor from outside. Such an alternative external UV light source configuration can be used in lieu of, or in combination with, a light source being disposed within electrode 84 such as light source 82.

Figure 4A:
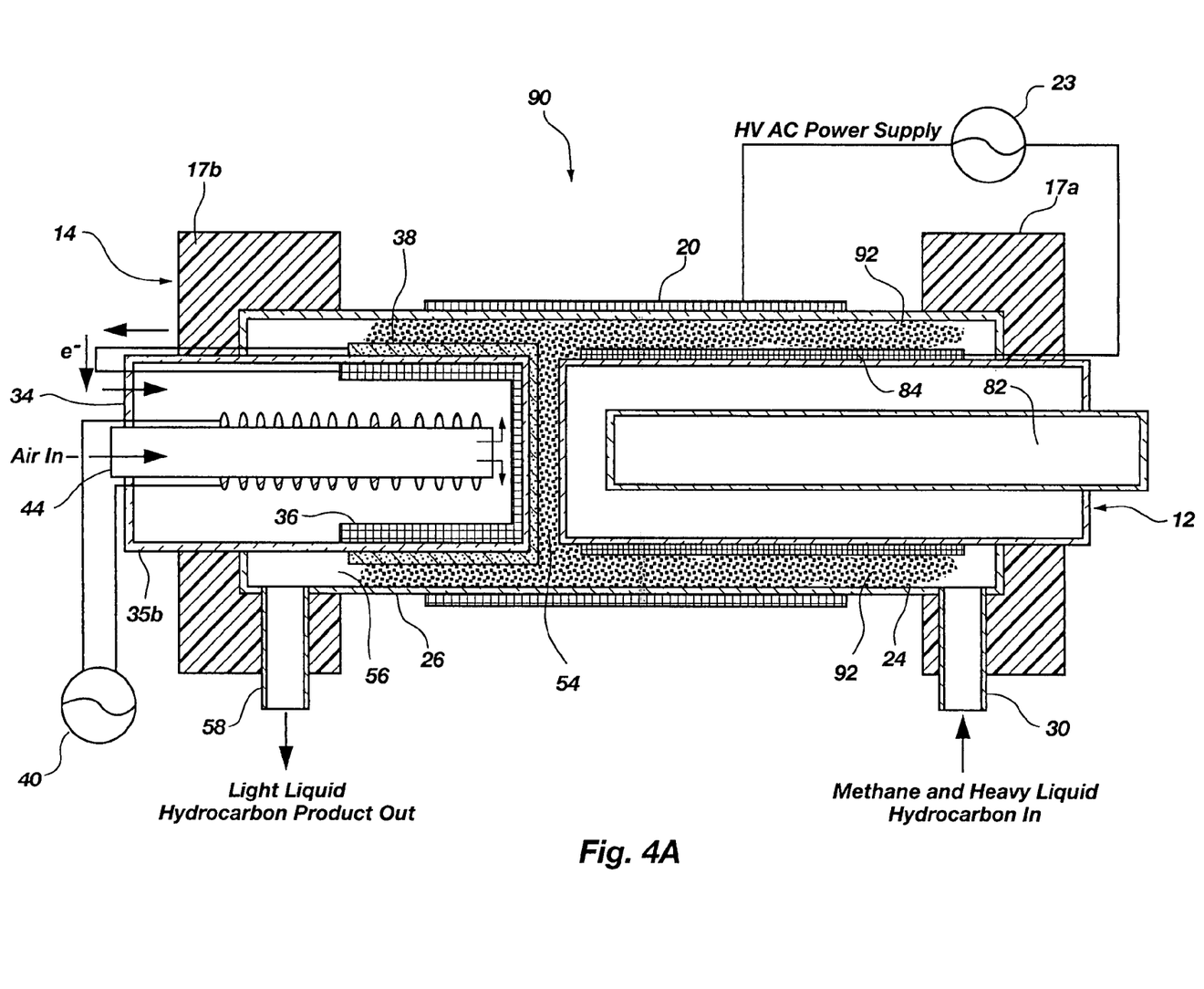
FIG. 4A is a schematic cross-sectional view of an apparatus for reactive conversion of hydrocarbons in accordance with a yet further embodiment of the invention.

In accordance with a yet further embodiment of the invention, FIG. 4A illustrates a chemical reactor 90 that can be used for gas to liquid conversion of hydrocarbons. The reactor 90 includes components similar to those discussed above with respect to reactor 80, being adapted to be used with a UV light source 82. Thus, reactor 90 generally comprises a dielectric barrier discharge plasma cell 12, and a solid oxide electrochemical cell 14.

The discharge plasma cell 12 of reactor 90 includes essentially the same components as discussed above for reactor 80, including an outer electrode 20 and an inner electrode 84, with a UV light source 82 positioned within electrode 84. The solid oxide electrochemical cell 14 of reactor 90 also includes essentially the same components as discussed above for reactor 80, including a mixed-conducting solid oxide electrolyte membrane tube 34, a porous anode 38 positioned on the exterior of membrane tube 34, and a porous cathode 36 positioned on the interior of membrane tube 34.

Figure 4B:
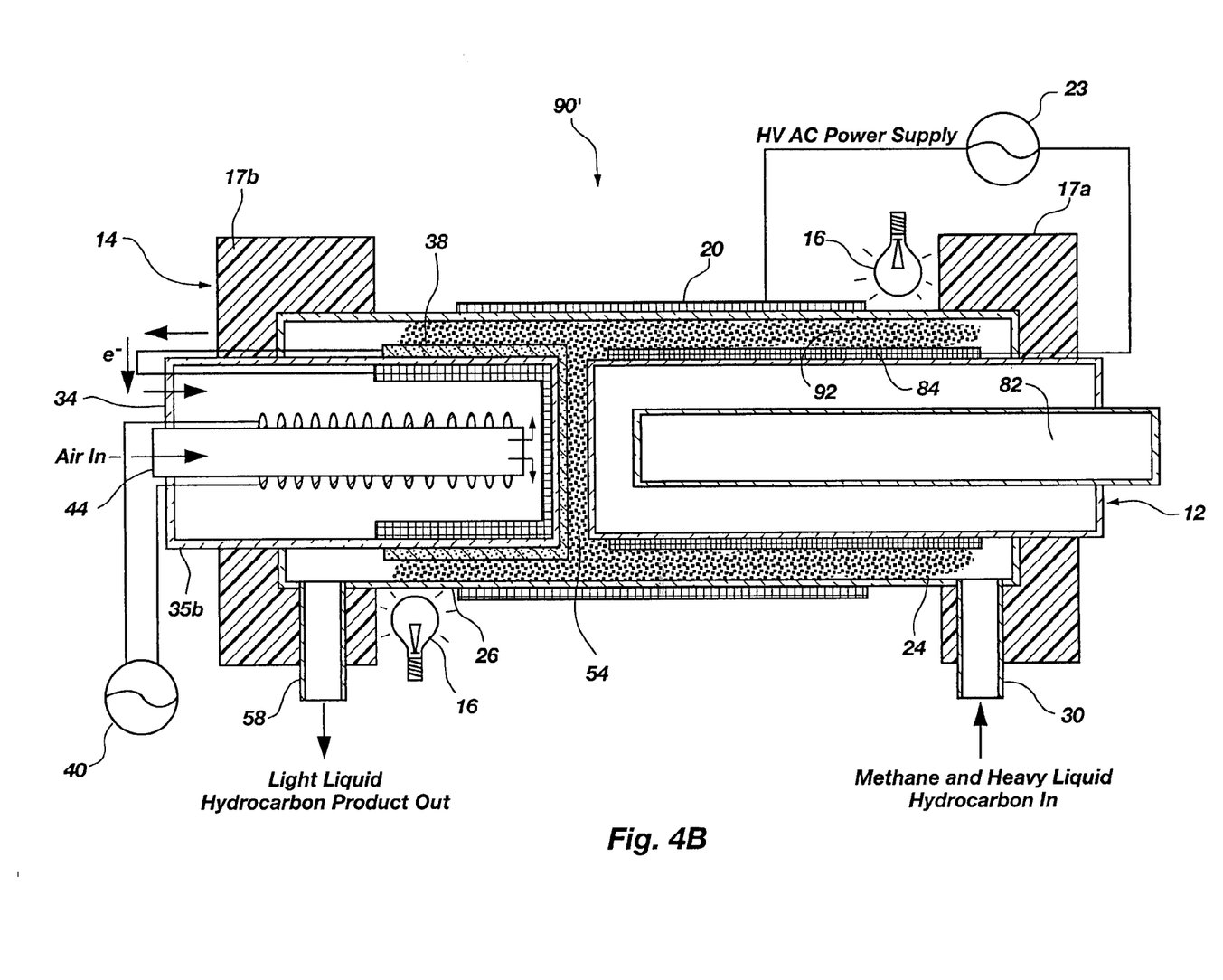
FIG. 4B is a schematic cross-sectional view of an apparatus for reactive conversion of hydrocarbons in accordance with yet another embodiment of the invention.

In addition, a packed bed catalyst 92 is disposed in reactor 90 and 90' within a passageway 24, a void 54, and passageway 56 as shown in FIGS. 4A and 4B respectively. The packed bed catalyst 92 can be used to control the types of products that reactor 90/90' yields. Suitable materials for packed bed catalyst 92 include those discussed previously for packed bed catalyst 70 of reactor 60. Thus, any hydrocracking catalysts, hydrogenating catalysts, or a combination of these catalysts can be used for natural gas conversion. The packed bed catalyst 92 may comprise a single catalytic zone configuration or a double zone configuration, as described previously for packed bed catalyst 70.

During operation of chemical reactor 80/80' or reactor 90, light from UV light source 82 transmits though electrode 84 into passageway 24 and/or UV light source(s) 16 transmit through the housing through the housing structure into passageway 24. The UV light enhances the energy level of the plasma in passageway 24 which is typically under atmospheric pressure. Simultaneously, the UV light also excites the molecular bonds of the reactants and more completely cracks the reactants to smaller molecular fragments. This higher energy state plasma and the UV light activate methane more efficiently and generate higher concentrations of hydrocarbon and hydrogen radicals. The UV light may also enhance the function of the solid oxide electrochemical cell 14, allowing more efficient production of oxygen radicals. During the reaction process, hydrogen is produced and hydrogenates the hydrocarbon fragments to form light hydrocarbon compositions. The light hydrocarbons may be significantly high in gasoline and diesel compositions. The oxygen radicals from solid oxide electrochemical cell 14 eliminate excess hydrogen radicals from the plasma as water molecules. The elimination of excess hydrogen radicals in the reactor promotes the polymerization of hydrocarbon radicals to heavier molecular hydrocarbons.

Because of higher energy and reactivity available from this UV-plasma coupled systems, the reactions therein may be sustainable below about 300° C. However, the temperature is not limited to this value and can assume a higher or lower value depending on the reaction requirements.

Alternatively, as depicted in FIG. 4B, a chemical reactor 90' can be provided with one or more UV light sources 16 which may be placed outside of the reactor housing when the reactor housing is UV transparent, allowing UV light to be transmitted into the reactor from outside as previously described with respect to alternative reactor 80'. As with reactor 80', an alternative external UV light source configuration can be used in lieu of, or in combination with, a light source being disposed within electrode 84 such as light source 82 as shown installed within reactor 90'.

The systems and methods of the present invention provide the benefit of improved conversion efficiencies over conventional technologies by increasing the conversion yield and reducing capital expenditures, as well as reducing facility operation and maintenance costs. The present invention further allows the oil and gas industries to significantly exploit under-utilized low value natural resources and convert them to high value products. In addition, the present invention allows for the exploitation of under-utilized low market value natural gas resources to meet current national energy needs. The present invention also reduces environmental pollutant precursors in the reaction products, and reduces long term environmental liability risks.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A method for direct conversion of hydrocarbons, the method comprising:
    directing a hydrocarbon feed through a dielectric barrier discharge plasma to produce reactive hydrocarbon species;
    subjecting the reactive hydrocarbon species to ultra-violet light;
    passing an oxygen containing gas through a mixed-conducting solid oxide electrolyte membrane tube, having a porous anode on an interior surface thereof and a porous cathode on an interior surface opposite from the porous anode, to thereby produce reactive oxygen-containing species;

reacting the hydrocarbon species with the oxygen-containing species to produce liquid products comprising fuel-type hydrocarbons and oxygenated hydrocarbons.

2. The method of claim 1, wherein the hydrocarbon species is reacted with the oxygen-containing species in the presence of a catalyst material.

3. The method of claim 1, wherein the fuel-type hydrocarbons comprise gasoline or diesel.

4. A method for direct conversion of hydrocarbons, the method comprising:
   directing a hydrocarbon feed through a dielectric barrier discharge plasma to produce reactive hydrocarbon species;
   passing an oxygen containing gas through a mixed-conducting solid oxide electrolyte membrane tube, having a porous anode on an exterior surface thereof and a porous cathode on an interior surface opposite from the porous anode, to thereby produce reactive oxygen-containing species;
   reacting the hydrocarbon species with the oxygen-containing species in the presence of a packed bed catalyst to produce liquid products comprising fuel-type hydrocarbons and oxygenated hydrocarbons.

5. The method of claim 4, wherein the fuel-type hydrocarbons comprise gasoline or diesel.

6. A method for direct conversion of hydrocarbons, the method comprising:
   directing a hydrocarbon feed through a dielectric barrier discharge plasma to produce reactive hydrocarbon species;
   passing an oxygen containing gas through a mixed-conducting solid oxide electrolyte membrane tube, having a porous anode on an exterior surface thereof and a porous cathode on an interior surface opposite from the porous anode, to thereby produce reactive oxygen-containing species;
   reacting the hydrocarbon species with the oxygen-containing species in the presence of ultraviolet light to produce liquid products comprising fuel-type hydrocarbons and oxygenated hydrocarbons.

7. The method of claim 6, wherein the hydrocarbon species is reacted with the oxygen-containing species in the presence of a packed bed catalyst.

8. The method of claim 6, wherein the fuel-type hydrocarbons comprise gasoline or diesel.

9. The method of claim 1, wherein the hydrocarbon species is reacted with the oxygen-containing species in the presence of at least one catalyst material selected from the group consisting of cobalt, nickel, platinum, rhenium, molybdenum, tungsten, palladium, NiMo, CoMo, and CoW.

10. The method of claim 1, wherein reacting the hydrocarbon species with the oxygen-containing species further comprises reacting the hydrocarbon species with the oxygen-containing species in the presence of ultra-violet light.

11. The method of claim 1, wherein passing an oxygen containing gas through a mixed-conducting solid oxide electrolyte membrane tube further comprises passing an oxygen containing gas through a mixed-conducting solid oxide electrolyte membrane tube in the presence of ultra-violet light.

12. The method of claim 4, wherein the packed bed catalyst comprises at least one catalyst material selected from the group consisting of cobalt, nickel, platinum, rhenium, molybdenum, tungsten, palladium, NiMo, CoMo, and CoW.

13. The method of claim 4, further comprising subjecting the reactive hydrocarbon species to ultra-violet light.

14. The method of claim 4, wherein reacting the hydrocarbon species with the oxygen-containing species in the presence of a packed bed catalyst further comprises reacting the hydrocarbon species with the oxygen-containing species in the presence of ultra-violet light.

15. The method of claim 6, wherein directing a hydrocarbon feed through a dielectric barrier discharge plasma further comprises directing a hydrocarbon feed through a dielectric barrier discharge plasma in the presence of ultra-violet light.

16. The method of claim 6, wherein passing an oxygen containing gas through a mixed-conducting solid oxide electrolyte membrane tube further comprises passing an oxygen containing gas through a mixed-conducting solid oxide electrolyte membrane tube in the presence of ultra-violet light.

17. The method of claim 6, wherein the hydrocarbon species is reacted with the oxygen-containing species in the presence of at least one catalyst material selected from the group consisting of cobalt, nickel, platinum, rhenium, molybdenum, tungsten, palladium, NiMo, CoMo, and CoW.

18. The method of claim 7, wherein the packed bed catalyst comprises at least one catalyst material selected from the group consisting of cobalt, nickel, platinum, rhenium, molybdenum, tungsten, palladium, NiMo, CoMo, and CoW.

* * * * *